United States Patent
D'Silva (12)

(10) Patent No.: US 6,550,955 B2
(45) Date of Patent: Apr. 22, 2003

(54) PROCESS FOR PRODUCING LIQUID DOSAGE FORMULATIONS OF MEDICINAL COMPOUNDS ON DEMAND FROM TABLETS AND CAPSULES USING A MIXING CUP WITH AN ABRASIVE INTERIOR SURFACE

(76) Inventor: Joe D'Silva, Ralph's Corner Offices, Suite 202, 2333 W. Main St., Lansdale, PA (US) 19446

(*) Notice: Subject to any disclaimer, the term of this patent is extended or adjusted under 35 U.S.C. 154(b) by 0 days.

(21) Appl. No.: 09/847,721

(22) Filed: May 2, 2001

(65) Prior Publication Data

US 2001/0053373 A1 Dec. 20, 2001

Related U.S. Application Data

(60) Provisional application No. 60/201,631, filed on May 3, 2000.

(51) Int. Cl.[7] ............................. B01F 3/12; B01F 7/16
(52) U.S. Cl. ................... 366/130; 366/306; 366/307; 366/314; 366/348; 604/403
(58) Field of Search ........................ 366/130, 314, 366/208–214, 306, 307, 341, 348; 206/219, 221; 220/568; 239/374; 604/416, 903

(56) References Cited

U.S. PATENT DOCUMENTS

| | | | |
|---|---|---|---|
| 2,352,205 A | | 6/1944 | Karlson |
| 3,397,867 A | | 8/1968 | Van't Hoff |
| 4,214,712 A | * | 7/1980 | Van Hoorn |
| 5,240,322 A | | 8/1993 | Haber et al. |
| 5,352,036 A | | 10/1994 | Haber et al. |
| 5,549,574 A | | 8/1996 | Townsend |
| 5,725,550 A | | 3/1998 | Micheler |
| 6,033,377 A | * | 3/2000 | Rasmussen et al. |
| 6,409,374 B1 | * | 6/2002 | Willat |

* cited by examiner

*Primary Examiner*—Charles E. Cooley
(74) *Attorney, Agent, or Firm*—Connolly Bove Lodge & Hutz LLP

(57) ABSTRACT

The invention relates to a process and device for making liquid dosage formulations from solid dosage forms, and the pharmaceutical compositions produced therefrom. The solid dosage forms are tablets and capsules. The device comprises a single-use mixing and dosing cup having an abrasive interior surface and may include a mixing blade attached to an external motor. A liquid dosage formulation is prepared by combining a solid dosage form of a pharmaceutical medicament and an aqueous diluent in the mixing and dosing cup. The solid dosage form is rapidly broken down into its constituent particulates using agitation, disintegration and abrasion. The resultant liquid mixture is flavored and thickened to suit the needs of individual patients. The mixing and dosing cup is designed to allow for the administration of the liquid formulation directly to the patient.

12 Claims, 4 Drawing Sheets

Mixing and Dosing Cup With Lid Displaying Two Types of Abrasive Surfaces

PROCESS FOR PRODUCING LIQUID DOSAGE FORMULATIONS OF MEDICINAL COMPOUNDS ON DEMAND FROM TABLETS AND CAPSULES USING A MIXING CUP WITH AN ABRASIVE INTERIOR SURFACE

This application is a continuation-in-part of U.S. Ser. No. 60/201,631, filed May 3, 2000, now abandoned, which is hereby incorporated by reference herein in its entirety.

FIELD OF THE INVENTION

The present invention relates to a process and a device for making liquid dosage formulations on demand from tablets and capsules, and the compositions produced therefrom.

BACKGROUND OF THE INVENTION

For several categories of patients, both human and veterinary, the use of tablets and capsules for administering medicinal compounds is not feasible. Some patients are unable to ingest tablets and capsules in a single and smooth swallowing motion, or lack the desire to ingest such dosage forms. Also, some tablets and capsules have an unpleasant taste or an uncomfortable or unpleasant size. Patient populations who encounter such problems include the elderly, particularly those in nursing homes, pediatric patients and patients who have encountered severe trauma due to surgery or involvement in accidents. Also, animals often will not or cannot swallow tablets or capsules. In the text that follows, the term "patient" refers to humans and animals.

In such situations, health care providers desire alternative dosage forms, especially liquids. For the above listed patient populations, liquid formulations are in general easier to swallow. If a liquid dosage alternative is commercially available, health care providers can avail themselves of the product for administration to their patients.

However, in many cases a liquid dosage form is not commercially available or, in some instances, the commercially available liquid dosage product is not suitable for the patient. In such circumstances, health care providers are forced to improvise and prepare liquid products in an extemporaneous fashion. Common approaches include grinding tablets in a mortar and pestle and adding the resultant powder to an excipient such as applesauce or a suitable fruit juice. In the case of capsules, the shells are separated and the enclosed powder added to an available excipient. The resultant mixture is then administered to the patient. Although this accomplishes the objective of providing a medicament formulation to the patient, the process does not guarantee the achievement of two important objectives, namely, delivery of the total dosage to the patient and avoidance of cross-contamination.

The first desired objective is the delivery of the total desired dose of the medicinal compound contained in the tablet or capsule to the patient. For example, some of the medicinal compound may be lost as the crushed tablet is transferred between a mortar and pestle to the dosing cups containing the excipient. In addition, improperly designed dosing procedures can result in the patient receiving less than the total dose. For example, the patient may not ingest all of the excipient/drug mixture. Medicinal compounds also are subject to decomposition. In certain instances, the decomposition accelerates when the material is in a liquid. The uncontrolled decomposition of the medicinal compound in an extemporaneously prepared liquid formulation could add to a reduction in the effective dose. In addition, the patient could be exposed to various undesired decomposition products.

Another problem with the present ad hoc approach to preparing liquid formulations is that some patients still resist taking the full dosage amount because of the unpleasant taste of the composition. For example, the active medicaments in cold medications often have a very unpleasant taste that is not easily masked by lightly flavored fruit drinks and sauces. Therefore, measures must be taken to flavor the liquid in some way so as to taste-mask the active medicament and prevent its rejection by the patient. If these drawbacks are not resolved, high degrees of patient compliance cannot be assured.

The second objective of the present invention is avoidance of medicament cross-contamination. The preparation of several extemporaneous formulations in a common environment demands the scrupulous cleaning and washing of the apparatus used in preparing the formulation. This is a difficult and cumbersome task especially for medicinal compounds that are not readily soluble in aqueous media. The cleaning requires well-documented research to ensure that the process is both complete and reproducible. Most health care providers do not have facilities and personnel to conduct the necessary research and experimentation. Cross-contamination can result in major side effects especially when the contaminant is a medicinal compound with a low therapeutic index.

In addition, the patients receiving these extemporaneously formulated products generally are those who would be harmed the most from cross-contamination. For example, pediatric and geriatric patients are more sensitive to small amounts of medicament, such as that present by contamination, than a typical adult patient. As a useful comparison, manufacturing operations in pharmaceutical companies often utilize safety factors of less than from $\frac{1}{100}^{th}$ to $\frac{1}{1000}^{th}$ of the human dose of a medicinal compound as a guideline in controlling cross-contamination between products. This low tolerance for cross-contamination is evidence of the acceptance in the pharmaceutical industry of the problems and risks associated with even small amounts of medicament cross-contamination.

The invention described herein provides an easy and convenient solution for providing extemporaneously compounded liquid products from tablets, capsules and other solid or gel pharmaceutical dosage forms (collectively "solid dosage forms"), preferably which are commercially available. Under the process of the invention, a health care provider or patient has the ability to administer a complete drug dose in a palatable liquid product and to eliminate cross-contamination. The compounding of the liquid formulation and the dosing of the resultant product are undertaken in a sanitary, reproducible and convenient fashion.

BRIEF SUMMARY OF THE INVENTION

The invention relates to a process and device for making liquid dosage formulations on demand from solid dosage forms, and the pharmaceutical compositions produced therefrom. The device comprises a mixing and dosing cup (1) having an abrasive interior surface (2). According to the process of the invention, a liquid dosage formulation is prepared by combining a solid dosage form of a pharmaceutical medicament and an aqueous diluent in a mixing and dosing cup having an abrasive surface, agitating the resulting mixture, and administering the resulting liquid dosage formulation to a patient in the mixing and dosing cup (1). The mixing and dosing cup (1) is a single-use cup, meaning it is not used again for pharmaceutical dosaging or mixing.

BRIEF DESCRIPTION OF THE DRAWINGS

FIG. 1 depicts a sampling of the types of abrasive surfaces (2) that could be employed separately or in combination in the design of the mixing and dosing cup (1).

FIG. 2 depicts a mixing blade (4) attached to a motor (5). The mixing blade (4), when agitated, causes contact between the solid dosage form and the abrasive surface (2) of the mixing and dosing cup (1).

DETAILED DESCRIPTION OF INVENTION

Figure 1:
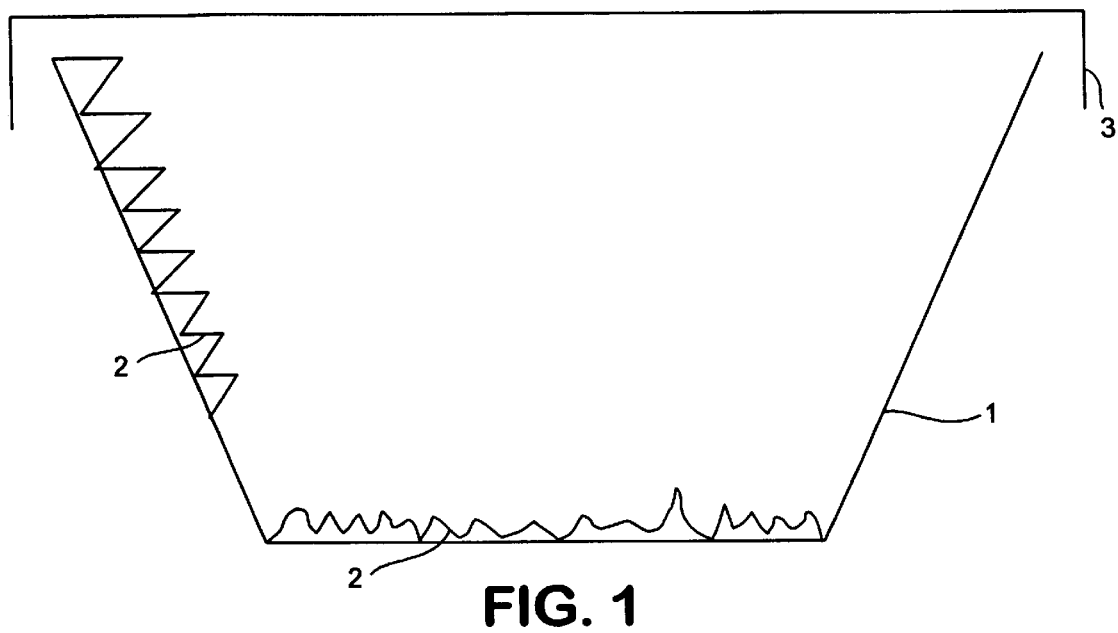
FIG. 1. Cross-section of a mixing and dosing cup (1) with lid (3) according to the invention.

Commercial pharmaceutical tablets and capsules contain particles of medicinal compound in a mixture of inert materials that are compressed or blended together. The inert materials include diluents such as lactose, binders such as microcrystalline cellulose, lubricants such as magnesium stearate, disintegrants such as modified starches, and coloring, flavoring and coating agents. The tablet or capsule is ingested into the stomach, where an aqueous environment causes the tablet or capsule coating to disintegrate or erode exposing the tablet or capsule core to the aqueous environment. Subsequently, in the stomach's aqueous environment, the tablet or capsule disintegrates into its particulate components allowing for the dissolution of the medicinal compound and its absorption into the blood stream.

According to the process of the invention, a solid dosage form at least partially is disintegrated ex vivo into its particulate constituents through physical and/or chemical means, such as abrasion, agitation or aqueous disintegration, and combinations thereof, and formulated into a liquid dosage formulation. The resultant liquid formulation when ingested into the stomach presents the medicinal compound to the gastrointestinal environment in a state similar to that encountered after some disintegration of a swallowed tablet. Because the medicament is being presented to the body in essentially the same physical and chemical form as it would be in after solid dosage ingestion and stomach degradation, the safety profiles from the administration of the compositions of the invention are expected to be substantially the same as those of the starting solid dosage form.

According to the process of the invention, a liquid dosage formulation is prepared from a solid dosage form of a pharmaceutical product on demand by at least partially disintegrating the solid dosage form through physical means, chemical means, or both physical and chemical means in the presence of an aqueous diluent. The solid dosage form, aqueous diluent and optionally one or more excipients are added to a mixing and dosing cup. "Aqueous diluent" refers to water, fruit juices, and other liquids containing at least about 5% water by weight, preferably at least about 30% water by weight, and most preferably at least about 50% water by weight. "Excipient" refers to pharmaceutically acceptable excipients as known to those of skill in the art. The mixture is agitated, for example, mechanically or manually, until the solid dosage form is sufficiently disintegrated, preferably until a mixture is obtained in which the mass median particle size diameter as measured by laser light diffraction is about 90 microns in size or less, yet more preferably of about 50 microns in size or less. The resulting liquid formulation is then administered to the patient in the same cup in which the mixing occurred. That cup is a single use cup. As used herein, "single use" cup means a cup that is not reused for medicinal dosaging or mixing. The liquid formulation is palatable and possesses the desired viscosity and volume for proper administration to the patient. The medicinal compound is chemically stable in the liquid formulation. Because the preparation of the liquid formulation is conducted using a single use dosing cup for each administration and the only surfaces to which the liquid formulation is exposed are those of the dosing cup, there is no possibility of cross-contamination from other medicaments or contaminants.

Preferably, one or more excipients are added to the medicinal compound. Preferably, the excipients are one or more of the following ingredients designed to enhance various features of the resulting liquid formulation: a) flavors to enhance the palatability; b) sweeteners to improve the taste; c) polymers to increase the viscosity; d) buffering agents to control the pH; e) preservatives to prevent microbial growth; f) antioxidants to reduce or eliminate oxidative decomposition; and g) agents to facilitate the delivery of the dose by enhancing drainage from the dosing cup during administration. Preferably, the excipients are provided as one or more discrete mixtures. In one preferred embodiment, each such excipient mixture is formulated for a specific quantity of a specific drug for desired taste and viscosity of the final liquid composition. Preferably, the mixture of excipients is provided as one or more compressed tablets, powder mixtures, pastes or solutions, and designed for a particular dosage of a particular medicament.

Figure 2:
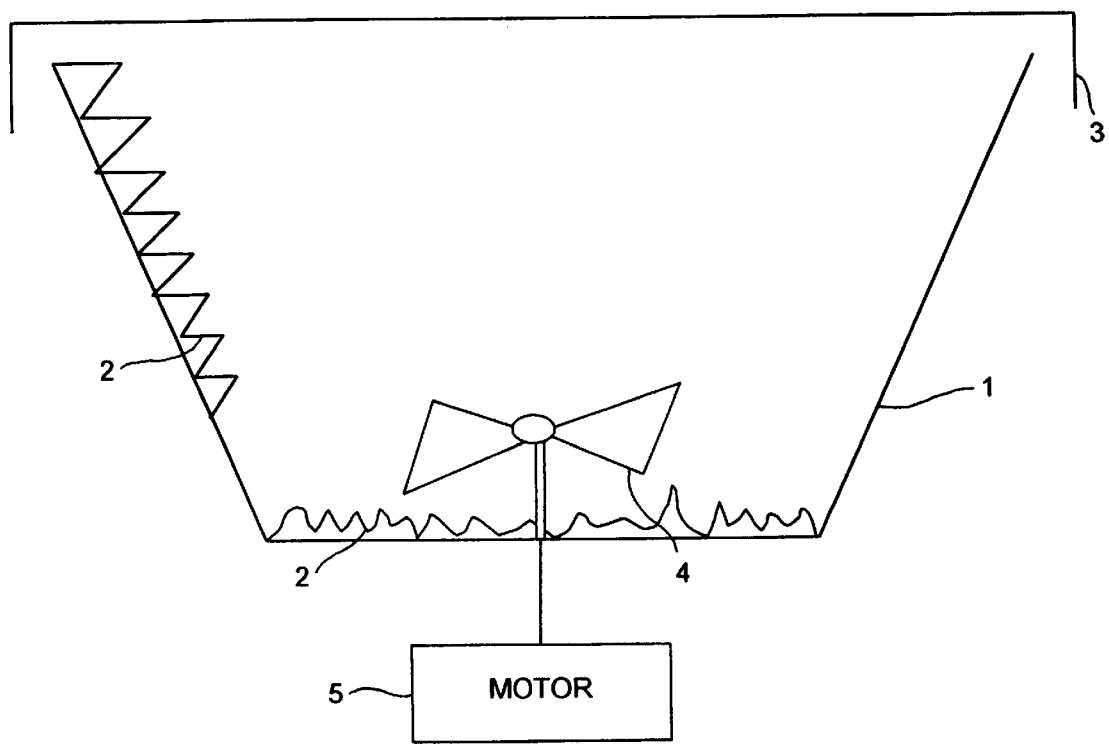
FIG. 2. Cross-section of a mixing and dosing cup (1) with lid (3) according to the invention.

In preferred embodiments, a specially designed mixing and dosing cup similar to those shown in FIG. 1 or 2 is used. This mixing and dosing cup is a single use cup that is used both to formulate the liquid composition and to administer a dose to the patient. In this way, cross-contamination by other medicaments is eliminated. Furthermore, the likelihood of the patient ingesting the entire dose is high because none of the medicament has been lost in inefficient transfers from formulating to dosing devices.

Such a cup is designed with internal abrasive surfaces. The cup has a suitable lid. Preferably, the cup is capable of being placed in a specially designed shaker that provides vigorous agitation to the contents placed within. The agitation can also be provided when appropriate via manual agitation of the cup and its contents. Preferably, the interior surface of the cup has a serrated and rough finish. The abrasive surface in combination with the agitation assists in a rapid disintegration of the solid dosage form into its particulate components and produces a desired small particle size.

The level of abrasiveness of the interior cup surface can vary depending on the amount of abrasion required for rapid disintegration to occur. The level of abrasiveness of the surface is designed to allow for the preparation of a liquid product with suitable palatability. The particle size of the suspended material should be small and the resulting formulation not be gritty in nature. The level of abrasiveness is also designed to minimize the time required to produce the liquid formulation. This will enable a health care provider to prepare formulations efficiently. To meet these functions, preferably the mixing and dosing cup of the invention has about 10% to about 99% of its interior surface area at an angle of 10° or greater tangent to the exterior surface of the cup. Preferably, the cup has about 50% to about 99% of its interior surface area at an angle of 30–90° tangent to the exterior surface of the cup, and more preferably, about 70% to about 99% of its interior surface is at a 35–90° tangent to the exterior surface of the cup. Preferably, the mixing and dosing cup contains about 5–20 ml of liquid, more preferably about 5–15 ml, and most preferably about 5–10 ml. The mixing and dosing cup and its lid may be made of any pharmaceutically acceptable, non-reactive material, preferably plastic, coated paper, or non-reactive metal, more preferably, polypropylene, polystyrene, polyethylene phthalate (PET), polyethylene, or combinations or copolymers thereof.

As a result of the centrifugal forces generated by mixing, the aqueous mixture has a tendency for a greater residence time during the mixing process in particular sections of the dosing cup. For example, the longest residence times noted in experiments using an orbital shaker were in areas towards the top of the cup, more particularly near the lip and at the lid. The abrasive surface will be preferably positioned in those areas of the dosing cup that provide for maximum contact between the tablet or capsule and the abrasive surface. This construction feature maximizes the efficiency of the abrasion process. In one preferred embodiment, the abrasive surface of the interior of the mixing and dosing cup is located primarily in the area of the cup in which the residence time during mixing of the solid dosage form is the longest. For example, for a process in which mixing is performed using an orbital shaker, the lid of the cup has an abrasive interior surface. Preferably, about 10% to about 99% of the interior surface area of the lid is at an angle of 10° or greater tangent to the exterior surface of the cup. More preferably, the lid has about 50% to about 99% of its interior surface area at an angle of 30°–90° tangent to the exterior surface of the cup, and still more preferably, about 70% to about 99% of its interior surface at an angle of 35°–90° tangent to the exterior surface of the cup.

The surface of the cup may be engineered to allow for maximum drainage of formulation while dispensing the liquid formulation. For example, the surface may have a non-stick coating, such as polytetrafluoroethylene, sold as Teflon® by DuPont, or wax. Also, in one preferred embodiment, the bottom of the cup is smooth, which encourages complete drainage.

According to the process of the invention, disintegration may be accomplished by any suitable type of physical agitation, for example, by manual shaking or mechanical shaking. Preferably, if a tablet is the starting material, water is added to the tablet before agitation to aid or cause disintegration.

In a preferred embodiment, a mechanical shaker is used that has a receptacle to accept the mixing and dosing cup and is able to provide intensive agitation to the contents of the cup, such as the cup depicted in FIG. 1. The energy provided by the agitation coupled with the abrasive surface of the dosing cup and the aqueous environment will allow for the rapid disintegration of the solid dosage form into its particulate constituents and the formation of the liquid dosage formulation. The shaker is preferably a commercially available shaker modified to receive and agitate the mixing and dosing cup. Some examples are orbital shakers, reciprocating shakers or Multi-Wrist™ shaker available from Lab-Line Instruments, Inc. In another preferred embodiment, a dosing cup (1) such as that depicted in FIG. 2 is employed. The mixing blade (4) is attached to an external motor (5) via a suitable coupling device. The motor (5) turns the mixing blade (4) causing the contents of the dosing cup (1) to be agitated. As a result, the tablet or capsule passes at a high velocity across the abrasive surfaces (2). The result is a disintegration of the solid-dosage formulation into small particles.

Preferably, the mixture of excipients contains polymers, which upon contact with the aqueous environment provide the product with a desirable viscosity. For some patients, a product with very low viscosity characteristics may not be a desirable option. A product with the consistency of a "pudding" may be easier to ingest, in particular for the elderly patient population. The option of producing products with low or enhanced viscosity can be maintained by making prepackaged mixtures of excipients available with varying levels of polymeric agents. In one preferred embodiment of the invention, the polymers added to the product provide the formulation with a thixotropic nature. In such a formulation, the viscosity of the product increases upon standing to provide the desired physical stability and thus maintain the homogeneity of the product. Upon providing energy input to the product via shaking, the viscosity of the product is reduced allowing for optimal dosing characteristics. When necessary, the mixture of excipients contains agents that control the pH of the liquid dosage product, such as buffers. This maintains the stability of the medicinal compounds within the final liquid formulation by providing conditions under which the decomposition of the medicinal compound is minimized, and/or the destabilization of the formulation is avoided.

In one embodiment, thickeners such as sodium carboxymethyl cellulose are added in amounts of from approximately 0.1% w/v to about 0.5% w/v of the total composition, and preferably from about 0.15% w/v to about 0.25% w/v and most preferably in an amount of about 0.20% w/v of the total formulation. Humectants are used to give the liquid greater viscosity and stability. Suitable humectants for the formulations of the present invention include glycerin, polyethylene glycol, propylene glycol and mixtures thereof. Preferably, glycerin is used and incorporated in an amount of from about 2.0% w/v to about 15% w/v and preferably in an amount of from about 4.0% w/v to about 8.0% w/v of the entire composition and most preferably in an amount of about 6.0% w/v of the total composition. Stabilizers such as sodium benzoate as a preservative and citric acid and sodium citrate as pH buffers are well known in the art and may be added in amounts as dictated by standard pharmacological practice.

Many medicinal compounds possess unpleasant taste characteristics. The flavors and sweeteners added to the product will assist in enhancing the palatability of the product. The flavors are selected to meet the requirements of specific patient populations. Suitable sweeteners for the compositions of the invention include water-soluble artificial sweeteners such as saccharin salts, cyclamate salts, acesulfame-K, monoammonium glycyrrhizinate and mixtures thereof. Other suitable sweetening agents include aspartame, sucrose, sucralose, protein based sweeteners such as thymidine, monellin and the like. In general, the effective amount of sweetener employed varies according to the type of sweetener used and the level of sweetness desired. Preferably, the amount is from about 0.01% w/v to about 5.0% w/v and more preferably from about 0.01% w/v to about 1.0% w/v of the liquid dosage formulation.

Sodium saccharin is a preferred sweetener and is incorporated in an amount of from about 0.01% w/v to about 0.5% w/v of the weight of the liquid dosage formulation.

The flavorings that may be used in the invention include those known to the skilled artisan, such as natural and artificial flavors. More specifically, the flavorings may be synthetic flavor oils and flavoring aromatics, and/or oils, oleo resins and extracts derived from plants, leaves, flowers, and fruits and combinations thereof. Examples of suitable flavorings include spearmint oil, cinnamon oil, oil of wintergreen (methyl salicylate), peppermint oil, clove oil, bay oil, eucalyptus oil, thyme oil, cedar leaf oil, oil of nutmeg, oil of sage, and oil of bitter almond. Also useful are artificial, natural or synthetic fruit flavors such as vanilla, and citrus oil, including lemon, orange, grape, lime and grapefruit and fruit essences including apple, pear, peach, strawberry, raspberry, cherry, plum, pineapple, and apricot. These flavorings may be used individually or in combinations with each other. Preferred flavors include peppermint, menthol, artificial vanilla, cinnamon derivatives, and various fruit flavors.

Flavorings such as aldehydes and esters including cinnamyl acetate, cinnamaldehyde, citral, diethylacetal, dihydrocarvyl acetate, eugenyl formate, and p-methylanisole may also be used. Generally, any flavoring or food additive described in "Chemicals Used in Food Processing" pub. 1274 by the National Academy of Sciences, pages 63–258 may be used.

Further examples of suitable aldehyde flavorings include acetaldehyde (apple); benzaldehyde (cherry, almond); cinnamic aldehyde (cinnamon); citral, i.e., alpha citral (lemon, lime); neral, i.e. beta citral (lemon, lime); decanal (orange, lemon); ethyl vanillin (vanilla, cream); heliotropine, i.e. piperonal (vanilla, cream); vanillin (vanilla, cream); alpha-amyl cinnamaldehyde (spicy fruity flavors); butyraldehyde (butter, cheese); valeraldehyde (butter, cheese); citronella (modifies, many types); decanal (citrus fruits); aldehyde C-8 (citrus fruits); aldehyde C-9 (citrus fruits); aldehyde C-12 (citrus fruits); 2-ethyl butyraldehyde (berry fruits); hexenal, i.e. trans-2 (berry fruits); tolyl aldehyde (cherry, almond); veratraldehyde (vanilla); 2,6-dimethyl-5-heptenal, i.e. melonal (melon); 2,6-dimethyloctanal (green fruit); and 2-dodecenal (citrus, mandarin); cherry; grape; and mixtures thereof. The amount of flavoring employed is normally a matter of preference subject to such factors as flavor type, individual flavor, and strength desired. Generally, flavors in amounts of about 0.05% to about 2.0% by weight of the total liquid dosage formulation are suitable and amounts of about 0.05% to 1.5% are preferred.

For veterinary products, flavorings appealing to the animal patient are desirable. An example is 3,7-dimethyl-1,6-octadien-3-ol (commonly known as "linalool"), preferably in an amount of between about 0.0001 to 0.001% by weight of the liquid dosage product, as disclosed in U.S. Pat. No. 4,294,857 to Fuller issued Oct. 13, 1981. Additional flavorings are disclosed in Furia et al., "Fenaroli's Handbook of Flavor Ingredients", CRC Press. Other examples of suitable veterinary flavorings are:

Anise
Bacon
Caramel
Celery
Cheese
Clover
Fish flavors such as salmon, sardine and tuna
Fish oils
Fruit flavors such as apples, banana, cherry, raspberry and strawberry
Garlic
Ginger
Lemon oil
Licorice
Liver
Meat flavors such as beef, chicken and lamb
Molasses
Onion
Parsley
Peanut butter
Milk powder
Tomato
Vanillin Preferably, the finished liquid dosage formulation comprises one or more of the following:
(1) a medicinal compound with the excipients used in the tablet or capsule formulation
(2) sweeteners such as sucrose, aspartame or saccharin
(3) buffering agents such as citrate, phosphate or acetate
(4) appropriate flavors, both natural and artificial
(5) anti-microbial preservatives such as benzoates, methyl paraben, propyl paraben and sorbic acid
(6) viscosity enhancers such as modified food starch, hydroxypropyl cellulose, hydroxypropyl methylcellulose, xanthan gum or sodium carboxymethyl cellulose
(7) antioxidants such as propyl gallate or sodium metabisulfite, and
(8) purified water.

If desired and the product characteristics allow for it, the final liquid dosage formulation is sub-divided into several unit doses employing dosing equipment such as oral syringes or the product is stored in appropriate conditions and doses withdrawn for use as required over a period of time.

Liquid formulations of combinations of medicinal compounds can be made by the process and device of the invention, and are also subjects of the invention. An example is a combination of acetaminophen, atropine, and midazolam. This combination is employed to sedate pediatric patients, to provide prophylactic pain relief, and to reduce the degree of aspiration. At present, a combination of injectables and commercially available syrups are employed. Under the process of the present invention, a formulation can be prepared by using the inventive methods to prepare a liquid formulation from solid dosage forms, and mixing thereto one or more commercially available liquid formulations of other desired medicaments. A liquid formulation of combinations of medicaments may be prepared also by placing the medicaments in solid dosage form or forms in the mixing and dosing cup, and agitating until the desired particle size is reached. Aqueous diluents may be added before and/or after agitation to provide the desired flavor, dosing volume, and consistency.

The following medicinal compounds are preferred examples of those that can be employed individually or in combination in the present invention:
Acetazolamide
Acetaminophen
Allopurinol
Amiodarone
Amoxicillin
Atenolol
Azathioprine
Baclofen
Captopril
Cephalosporins, particularly Cefquinome and Ceftiofur
Cimetidine
Clavamox
Clomipramine
Clonazepam
Clonidine
Cyprohetadine
Cyclosporine
Dilitiazem
Doxycycline
Enalapril
Etodolac
Flucytosine
Hydrazaline
Hydroxycholoroquine
Hydrochlorthiazide Ibuprofen
Isradipine
Leflunomide
Levothyroxine sodium
Lorazepam
Macrolide
Metolazone
Metronidazole
Misoprostol
Mitotane
Mycophenolate
Pancrelipase/Panokase
Pseudoephedrine hydrochloride
Quinolones, particularly Danofloxacin and Enrofloxacin
Ranitidine
Rifampin
Selegiline
Spironolactone
Sucralaftate
Sulfamethoxazole/Trimethoprim (sold as Bactrim®)
Tacrolimus
Tetracyclines
Thioguanine
Ursodiol
8a-azalide
Vitamin supplements Of these, the more preferred compounds are the following:
Acetazolamide
Allopurinol
Amoxicillin
Captopril
Metronidazole
Rifampin
Spironolactone For veterinary use, the following medicinal compounds are preferred examples of those that can be employed individually or in combination in the present invention:
Amitryptyline hydrochloride
Amoxicillin
Amoxicillin trihydrate and clavulanate potassium combination
Cephalexin
Cephalexin hydrochloride
Clindamycin hydrochloride
Doxycycline hyclate
Doxycycline monohydrate
Enrofloxacin
Griseofulvin
Metoclopramide monohydrochloride monohydrate
Methimazole
Metronidiazole
Pseudoephedrine hydrochloride
Trimethoprim and sulfadiazine combination Of these, the more preferred compounds are the following:
Amoxicillin
Amoxicillin trihydrate and clavulanate potassium combination
Cephalexin
Clindamycin hydrochloride
Doxycycline monohydrate
Enrofloxacin
Methimazole
Trimethoprim and sulfadiazine combination These compounds may be obtained commercially in solid dosage forms or may be prepared by using methods available in the art. Solid dosage forms for immediate release are preferable for the present invention.

Additionally, other medicinal compounds formulated as solid dosage forms may be used in the present invention, as would be apparent to one of skill in the art.

The following classes of patients and health-care providers can benefit from this invention:

Patients who have difficulty in swallowing: This group includes patients suffering from stroke, esophageal cancers, oral motor impairments, Alzheimer's disease, Parkinson's syndrome, sore throat and status post tonsillectomy.

Patients who cannot swallow: This group includes patients with nasogastric intubations, gastrostomy and jejunostomy, post-operative patients, patients in Intensive Care Units and Cardiac Care Units and comatose patients.

Patients who will not swallow: This group includes pediatric patients and patients with psychiatric problems.

Ailing pets and farm animals and their health-care providers: This group includes the ailing animals, particularly livestock and pets, veterinarians, pharmacists, pet owners and farmers.

The invention is also directed to methods of treating the patients and the disorders mentioned above by administering liquid dosage formulations.

EXAMPLES

Example 1

The process of producing liquid formulations was demonstrated by using the following commercial solid dosage products as examples:
200 mg tablets of ibuprofen
600 mg tablets of ibuprofen
500 mg tablets of acetaminophen
30 mg tablets of pseudoephedrine hydrochloride
250 mg capsule of amoxicillin For the tablets, one tablet was placed in 15 ml of distilled water at room temperature. The condition of each tablet was observed after intervals of 2, 5 and 10 minutes. The tablets were not fully disintegrated. Samples were observed to be in various stages of disintegration. This process is based on the absorption of aqueous fluids into the tablet resulting in a swelling of the disintegrants included therein. The abrasion process described in this application is designed to accomplish the disintegration process and efficiently reduce the particle size of the resulting solids. The process consists of the tablets or their components being repeatedly exposed to an abrasive surface in the mixing and dosing cup at high velocities. A demonstration of the effectiveness of this process was undertaken as follows. Samples of the tablets that were exposed to the aqueous conditions listed above were gradually rubbed across coarse grain number 60 sandpaper. The sandpaper surface emulates the abrasive surface that will be designed within the mixing and dosing cup. Rubbing a tablet core across sandpaper caused it to disintegrate rapidly into its constituent particles. This result demonstrates that the process within the specially designed mixing and dosing cup is feasible. The final process will employ high velocities and provide greater contact of the tablet and its constituents with the abrasive surface. The higher energy input and enhanced contact will ensure that the disintegration process that has proven to be feasible in manual operations is completed more efficiently using the specially designed mixing and dosing cups and using mechanical mixers. In a preferred embodiment of the invention, the disintegration primarily will be accomplished by abrasion. By using physical abrasion, disintegration is much more rapid than when using aqueous methods alone, and the process can produce a superior product with a desirable small particle size of suspended solids.

The use of an abrasive surface is important when capsules are employed. Capsule shells are made of gelatin, which upon prolonged exposure to water become hydrated. The hydrated shells are pliable and slippery, and are difficult to rupture to release their medicament contents. However, when dry, the shells are brittle and susceptible to being ruptured and disintegrated by an abrasive surface.

This was demonstrated with samples of a 250 mg amoxicillin capsule. Samples were placed in 15 ml of water and withdrawn after a period of a few seconds, one minute and five minutes. The samples were then gradually rubbed across Coarse #60 sandpaper. The sample exposed to aqueous conditions for a few seconds was found to rupture easily releasing the contents of amoxicillin. Samples exposed to aqueous environments for one and five minutes were slippery and very pliable and were less responsive to the abrasive surface. Preferably, when capsules are used in the process of the invention, the abrasive mechanism will be employed with a dry capsule shell, such as by agitating the capsule alone in the mixing and dosing cup without any liquid present. An aqueous diluent and any desired excipients are added after capsule disintegration is substantially complete. When aqueous excipients are included with a capsule in a mixing and dosing cup and then agitation begins, preferably the agitation is initiated without delay to prevent the capsule shell from hydrating and becoming pliable and slippery.

Example 2

The following formulations were produced using the techniques described above. In each formulation, the medicinal compound used is a generic brand tablet formulation.

| Formulation 1: | |
|---|---|
| Ibuprofen | 300 mg |
| Corn Starch | 116 mg |
| Sucrose | 1.5 g |
| Imitation Rum Flavor | 1.3 ml |
| Vanilla Extract | 0.6 ml |
| Distilled Water | q.s. to 10.0 ml |

(1. Corn Starch was added as a 4% w/v mixture in water. The mixture was heated and cooled prior to addition to the formulation; 2. Sucrose was added as brown sugar)

| Formulation 2: | |
|---|---|
| Ibuprofen | 300 mg |
| Corn Starch | 140 mg |
| Calcium Saccharin | 18 mg |
| Lemon Extract | 2.5 ml |
| Distilled Water | q.s. to 10.0 ml |

(Corn Starch was added as a 4% w/v mixture in water. The mixture was heated and cooled prior to addition to the formulation)

| Formulation 3: | |
|---|---|
| Ibuprofen | 300 mg |
| Corn Starch | 140 mg |
| Calcium Saccharin | 18 mg |
| Orange Extract | 2.5 ml |
| Distilled Water | q.s. to 10.0 ml |

(Corn Starch was added as a 4% w/v mixture in water. The mixture was heated and cooled prior to addition to the formulation)

| Formulation 4: | |
|---|---|
| Ibuprofen | 300 mg |
| Distilled Water | 3.0 ml |
| Chocolate Syrup | q.s. 10.0 ml |

(Chocolate Syrup contains high fructose corn syrup, sucrose, corn syrup, cocoa, potassium sorbate, sodium chloride, mono and diglycerides from vegetable oil, polysorbate 60, xanthan gum, vanillin and water)

| Formulation 5: | |
|---|---|
| Pseudoephedrine Hydrochloride | 30 mg |
| Distilled Water | 3.0 ml |
| Chocolate Syrup | q.s. 10.0 ml |

(Chocolate Syrup contains high fructose corn syrup, sucrose, corn syrup, cocoa, potassium sorbate, sodium chloride, mono and diglycerides from vegetable oil, polysorbate 60, xanthan gum, vanillin and water)

| Formulation 6: | |
|---|---|
| Amoxicillin | 250 mg |
| Corn Starch | 308 mg |
| Dried Beef Bouillon | 2 g |
| Distilled Water | q.s. to 10.0 ml |

(1. Corn Starch was added as a 4% w/v mixture in water. The mixture was heated and cooled prior to addition to the formulation; 2. Dried Beef Bouillon contains sodium chloride, hydrolyzed vegetable protein, corn syrup solids, sugar, beef fat, monosodium glutamate, dextrose, onion powder, garlic powder, caramel color, natural flavorings, disodium guanylate, disodium inosinate, partially hydrogenated vegetable oil and artificial color)

| Formulation 7: | |
|---|---|
| Pseudoephedrine Hydrocholride | 30 mg |
| Corn Starch | 195 mg |
| Dried Beef Bouillon | 2 g |
| Distilled Water | q.s. to 10.0 ml |

(1. Corn Starch was added as a 4% w/v mixture in water. The mixture was heated and cooled prior to addition to the formulation; 2. Dried Beef Bouillon contains sodium chloride, hydrolyzed vegetable protein, corn syrup solids, sugar, beef fat, monosodium glutamate, dextrose, onion powder, garlic powder, caramel color, natural flavorings, disodium guanylate, disodium inosinate, partially hydrogenated vegetable oil and artificial color)

Example 3

The following table (Table 1) lists compositions of excipient mixtures that may be formulated and use in the present invention. The table lists human and veterinary formulations. The table lists the excipients that will be employed in an aqueous environment in conjunction with active ingredients from one or more tablets or capsules.

TABLE 1

| INGREDIENT | % w/v in distilled water (except where noted) | | | | | | | | | | |
|---|---|---|---|---|---|---|---|---|---|---|---|
| Sucrose | 30 | — | — | — | 30 | — | — | — | 5 | — | — |
| Sodium Saccharin | — | 0.25 | 0.25 | — | — | 0.25 | — | — | — | — | 0.25 |
| Sodium Carboxymethyl Cellulose | — | — | 1 | — | — | 1 | — | — | — | — | — |
| Xanthan Gum | 0.3 | 0.3 | — | — | — | — | 0.6 | — | — | 0.3 | — |
| Modified Corn Starch | — | — | — | — | — | — | — | 3 | 2 | — | 2 |
| Glycerol | — | — | — | — | — | 6 | 6 | — | — | — | — |
| Vanilla Extract | 6[a] | — | 6[a] | — | 6[a] | — | — | — | — | 3[a] | — |
| Orange Extract | — | 10[a] | — | — | 5[a] | — | — | — | — | — | — |
| Lemon Extract | — | — | — | — | — | 10[a] | — | — | — | — | 10[a] |
| Chocolate Syrup | — | — | — | 50[a] | — | — | — | — | — | 30[a] | — |
| Caramel | — | — | — | — | — | — | — | — | 10 | — | — |
| Dried Chicken Bouillon | — | — | — | — | — | — | 5 | — | — | — | — |
| Dried Beef Bouillon | — | — | — | — | — | — | — | 5 | 5 | — | — |

[a]Listed as v/v

Example 4

The differences in the particle size characteristics generated by a process using abrasion and a process employing a mortar and pestle were demonstrated with a commercially available 200 mg tablet of ibuprofen as follows.

Figure 3:
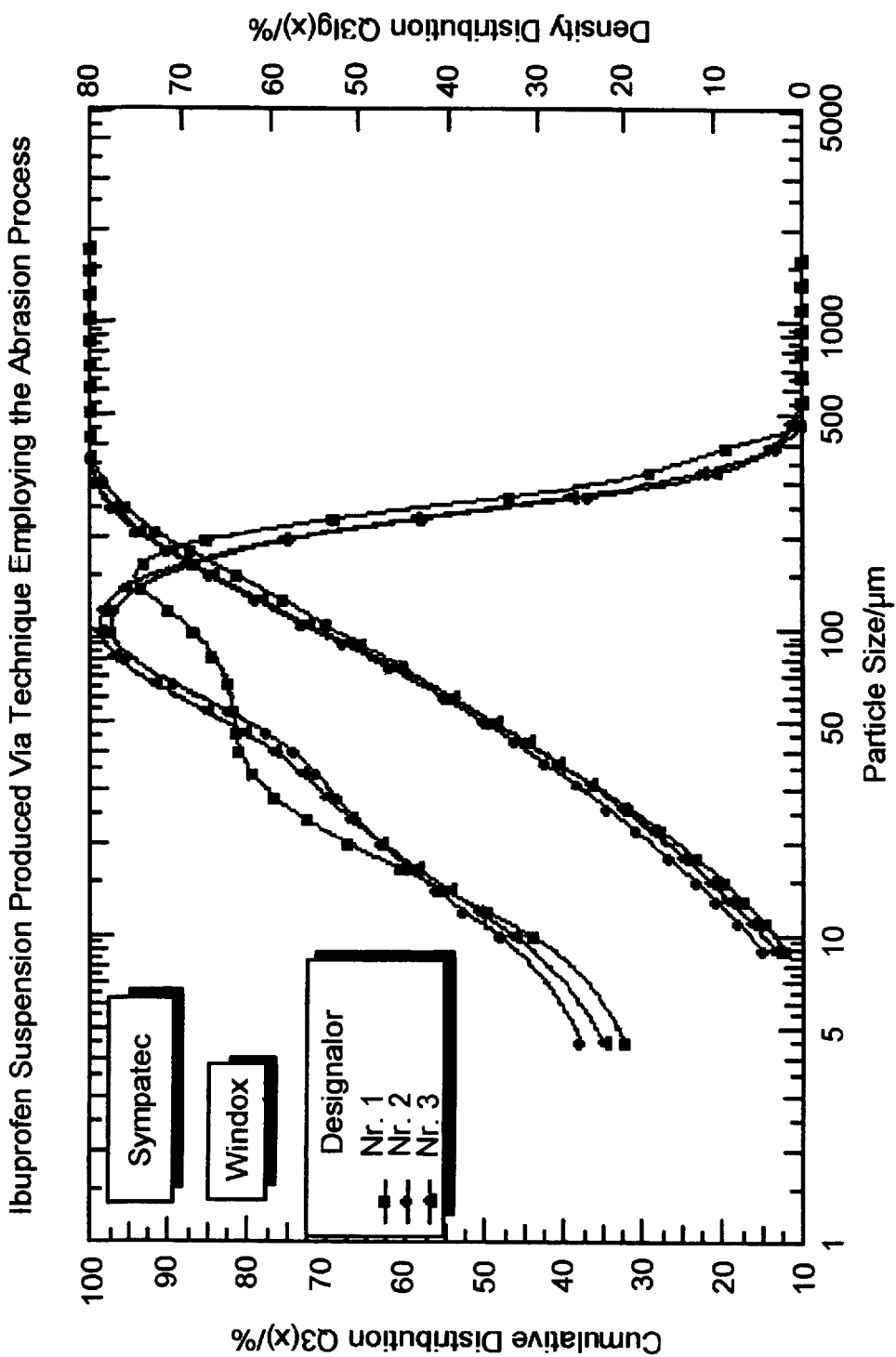
FIG. 3. Particle size distribution of ibuprofen suspension produced using an abrasion process.

A tablet was allowed to stand in 10 ml of distilled water for 2 minutes. The residual tablet core was rubbed across Coarse #60 sandpaper to cause complete disintegration. The material was returned to the aqueous environment and the mixture was well agitated. This experiment was performed three times. The particle size of the resultant powder is shown in Tables 2, 3 and 4 and in FIG. 3.

TABLE 2

Trial #1
Sympatec HELOS (H0862) & CUVETTE: IBP in aq. suspension
16:02:55,8500 HRLD (V 3.2 Rel. 4)

| x0/μm | Q3/% | x0/μm | Q3/% | x0/μm | Q3/% | x0/μm | Q3/% |
|---|---|---|---|---|---|---|---|
| 9.0 | 11.8 | 37.0 | 40.7 | 150.0 | 81.2 | 610.0 | 100.0 |
| 11.0 | 14.4 | 43.0 | 44.8 | 180.0 | 87.1 | 730.0 | 100.0 |
| 13.0 | 16.9 | 50.0 | 48.9 | 210.0 | 91.5 | 870.0 | 100.0 |
| 15.0 | 19.4 | 60.0 | 54.0 | 250.0 | 95.5 | 1030.0 | 100.0 |
| 18.0 | 23.0 | 75.0 | 60.2 | 300.0 | 98.1 | 1230.0 | 100.0 |
| 22.0 | 27.4 | 90.0 | 65.4 | 360.0 | 99.4 | 1470.0 | 100.0 |
| 26.0 | 31.4 | 105.0 | 70.0 | 430.0 | 100.0 | 1750.0 | 100.0 |
| 31.0 | 35.9 | 125.0 | 75.4 | 510.0 | 100.0 | | | x10 = 7.7 μm;
x50 = 52.2 μm;
x90 = 199.8 μm
x16 = 12.3 μm;
x84 = 164.3 μm;
x99 = 343.0 μm
Sv = 0.282 m$^2$/cm$^3$;
Sm = 2.15E + 03 cm$^2$/g;
copt = 9.89%

TABLE 3

Trial #2
Sympatec HELOS (H0862) & CUVETTE: IBP in aq. suspension
16:17:04,3400 HRLD (V 3.2 Rel. 4)

| x0/μm | Q3/% | x0/μm | Q3/% | x0/μm | Q3/% | x0/μm | Q3/% |
|---|---|---|---|---|---|---|---|
| 9.0 | 14.8 | 37.0 | 42.3 | 150.0 | 84.7 | 610.0 | 100.0 |
| 11.0 | 17.7 | 43.0 | 46.0 | 180.0 | 90.1 | 730.0 | 100.0 |
| 13.0 | 20.4 | 50.0 | 50.0 | 210.0 | 94.0 | 870.0 | 100.0 |
| 15.0 | 23.0 | 60.0 | 55.1 | 250.0 | 97.2 | 1030.0 | 100.0 |
| 18.0 | 26.5 | 75.0 | 61.9 | 300.0 | 99.1 | 1230.0 | 100.0 |
| 22.0 | 30.6 | 90.0 | 67.9 | 360.0 | 99.8 | 1470.0 | 100.0 |
| 26.0 | 34.2 | 105.0 | 73.0 | 430.0 | 100.0 | 1750.0 | 100.0 |
| 31.0 | 38.2 | 125.0 | 78.9 | 510.0 | 100.0 | | | x10 = 6.3 μm;
x50 = 50.0 μm;
x90 = 179.4 μm
x16 = 9.8 μm;
x84 = 146.9 μm;
x99 = 298.3 μm
Sv = 0.318 m$^2$/cm$^3$;
Sm = 2.43E + 03 cm2/g;
copt = 45.32%

TABLE 4

Trial #3
Sympatec HELOS (H0862) & CUVETTE: IBP in aq. suspension
16:21:37,5400 HRLD (V 3.2 Rel. 4)

| x0/μm | Q3/% | x0/μm | Q3/% | x0/μm | Q3/% | x0/μm | Q3/% |
|---|---|---|---|---|---|---|---|
| 9.0 | 13.3 | 37.0 | 40.6 | 150.0 | 84.2 | 610.0 | 100.0 |
| 11.0 | 16.0 | 43.0 | 44.5 | 180.0 | 89.6 | 730.0 | 100.0 |
| 13.0 | 18.7 | 50.0 | 48.6 | 210.0 | 93.5 | 870.0 | 100.0 |
| 15.0 | 21.1 | 60.0 | 53.9 | 250.0 | 96.8 | 1030.0 | 100.0 |
| 18.0 | 24.5 | 75.0 | 60.9 | 300.0 | 98.8 | 1230.0 | 100.0 |
| 22.0 | 28.6 | 90.0 | 67.0 | 360.0 | 99.7 | 1470.0 | 100.0 |
| 26.0 | 32.3 | 105.0 | 72.2 | 430.0 | 99.9 | 1750.0 | 100.0 |
| 31.0 | 36.3 | 125.0 | 78.2 | 510.0 | 100.0 | | | x10 = 6.9 μm;
x50 = 52.7 μm;
x90 = 183.0 μm;
x16 = 11.0 μm;
x84 = 149.4 μm;
x99 = 313.7 μm
Sv = 0.299 m$^2$/cm$^3$;
Sm = 2.28E + 03 cm$^2$/g;
copt = 28.56%

Figure 4:
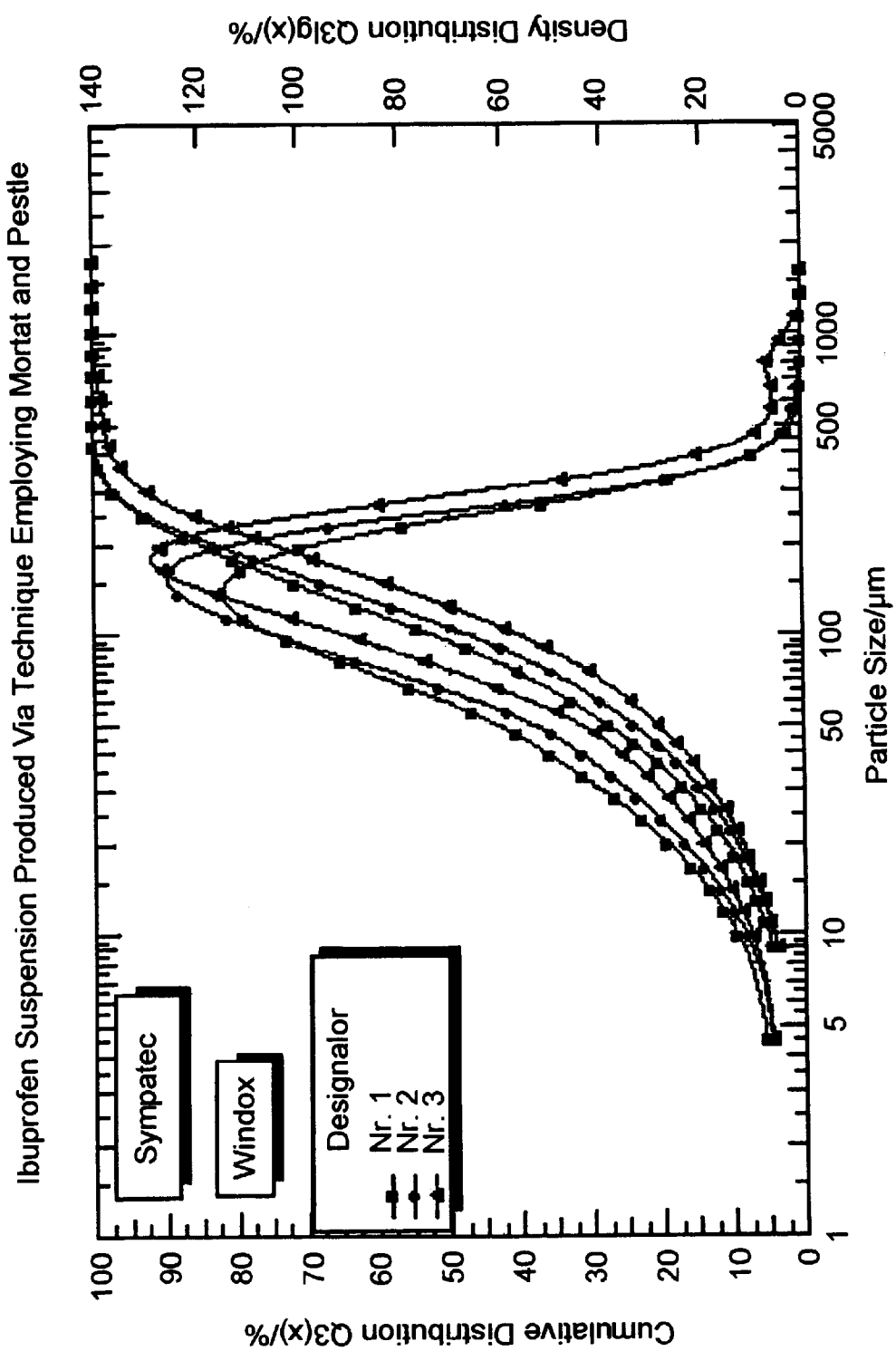
FIG. 4. Particle size distribution of ibuprofen suspension produced using a technique employing a mortar and pestle.

A tablet was crushed using a mortar and pestle. The resultant powder was incorporated into distilled water for evaluation of the particle size. This experiment was performed three times. The particle size of the resultant powder is shown in Tables 5, 6 and 7 and in FIG. 4.

TABLE 5

Trial #1
Sympatec HELOS (H0862) & CUVETTE: IBP in water
16:54:03 HRLD (V 3.2 Rel. 4)

| x0/μm | Q3/% | x0/μm | Q3/% | x0/μm | Q3/% | x0/μm | Q3/% |
|---|---|---|---|---|---|---|---|
| 9.0 | 4.5 | 37.0 | 20.5 | 150.0 | 71.6 | 610.0 | 100.0 |
| 11.0 | 5.6 | 43.0 | 23.8 | 180.0 | 80.4 | 730.0 | 100.0 |
| 13.0 | 6.7 | 50.0 | 27.5 | 210.0 | 87.0 | 870.0 | 100.0 |
| 15.0 | 7.9 | 60.0 | 32.7 | 250.0 | 92.9 | 1030.0 | 100.0 |
| 18.0 | 9.7 | 75.0 | 40.2 | 300.0 | 97.0 | 1230.0 | 100.0 |
| 22.0 | 12.0 | 90.0 | 47.4 | 360.0 | 99.1 | 1470.0 | 100.0 |
| 26.0 | 14.3 | 105.0 | 54.2 | 430.0 | 99.8 | 1750.0 | 100.0 |
| 31.0 | 17.2 | 125.0 | 62.6 | 510.0 | 100.0 | | |

$x10 = 18.6$ μm;
$x50 = 95.7$ μm;
$x90 = 230.2$ μm
$x16 = 29.0$ μm;
$x84 = 196.4$ μm;
$x99 = 358.6$ μm;
$Sv = 0.153$ m$^2$/cm$^3$;
$Sm = 1.17E + 03$ cm$^2$/g;
$copt = 36.14\%$

TABLE 6

Trial #2
Sympatec HELOS (H0862) & CUVETTE: IBP in water
16:58:46,6900 HRLD (V 3.2 Rel. 4)

| x0/μm | Q3/% | x0/μm | Q3/% | x0/μm | Q3/% | x0/μm | Q3/% |
|---|---|---|---|---|---|---|---|
| 9.0 | 3.8 | 37.0 | 17.8 | 150.0 | 67.5 | 610.0 | 100.0 |
| 11.0 | 4.7 | 43.0 | 20.7 | 180.0 | 77.4 | 730.0 | 100.0 |
| 13.0 | 5.7 | 50.0 | 23.9 | 210.0 | 85.1 | 870.0 | 100.0 |
| 15.0 | 6.8 | 60.0 | 28.5 | 250.0 | 92.2 | 1030.0 | 100.0 |
| 18.0 | 8.3 | 75.0 | 35.5 | 300.0 | 96.8 | 1230.0 | 100.0 |
| 22.0 | 10.3 | 90.0 | 42.4 | 360.0 | 98.9 | 1470.0 | 100.0 |
| 26.0 | 12.4 | 105.0 | 49.2 | 430.0 | 99.6 | 1750.0 | 100.0 |
| 31.0 | 14.9 | 125.0 | 57.8 | 510.0 | 99.9 | | |

$x10 = 21.3$ μm;
$x50 = 106.9$ μm;
$x90 = 237.7$ μm
$x16 = 33.3$ μm;
$x84 = 205.7$ μm;
$x99 = 371.0$ μm
$Sv = 0.137$ m$^2$/cm$^3$;
$Sm = 1.04E + 03$ cm$^2$/g;
$copt = 32.21\%$

TABLE 7

Trial #3
Sympatec HELOS (H0862) & CUVETTE: IBP in water
17:06:23,1700 HRLD (V 3.2 Rel. 4)

| x0/μm | Q3/% | x0/μm | Q3/% | x0/μm | Q3/% | x0/μm | Q3/% |
|---|---|---|---|---|---|---|---|
| 9.0 | 3.7 | 37.0 | 15.5 | 150.0 | 58.6 | 610.0 | 98.7 |
| 11.0 | 4.6 | 43.0 | 17.8 | 180.0 | 68.6 | 730.0 | 99.2 |
| 13.0 | 5.5 | 50.0 | 20.5 | 210.0 | 77.1 | 870.0 | 99.7 |
| 15.0 | 6.4 | 60.0 | 24.3 | 250.0 | 85.7 | 1030.0 | 100.0 |
| 18.0 | 7.7 | 75.0 | 30.2 | 300.0 | 92.3 | 1230.0 | 100.0 |
| 22.0 | 9.4 | 90.0 | 36.0 | 360.0 | 96.1 | 1470.0 | 100.0 |
| 26.0 | 11.0 | 105.0 | 41.9 | 430.0 | 97.7 | 1750.0 | 100.0 |
| 31.0 | 13.1 | 125.0 | 49.5 | 510.0 | 98.3 | | |

$x10 = 23.5$ μm;
$x50 = 126.4$ μm;
$x90 = 282.6$ μm
$x16 = 38.4$ μm;
$x84 = 242.0$ μm;
$x99 = 685.6$ μm
$Sv = 0.126$ m$^2$/cm$^3$;
$Sm = 964$ cm$^2$/g;
$copt = 48.42\%$ Particle size evaluation was undertaken using Laser Light Diffraction technique. The particle size is estimated via the mass median diameter as enumerated by the $10^{th}$, $50^{th}$ and $90^{th}$ percentile values. Following the process of the invention, the particle size values averaged over three experiments are 7, 52 and 187 microns for $10^{th}$, $50^{th}$ and $90^{th}$ percentiles respectively. Following grinding with a mortar and pestle, the particle size values averaged over three experiments are 21, 110, and 250 microns respectively for the same percentiles. Thus, the data demonstrates that the process of the invention produces a product with a smaller particle size.

Although the present invention has been described in terms of various embodiments, it is not intended that the invention be limited to those embodiments. Modification within the spirit of the invention will be apparent to those skilled in the art.

I claim:

1. A method for the preparation of a liquid dosage formulation from a solid dosage form of a medicinal compound and an aqueous diluent comprising: combining the solid dosage form and the aqueous diluent in a single-use mixing and dosing cup having an abrasive interior surface and mixing to form a liquid dosage formulation.

2. The method of claim 1 wherein about 10% to about 99% of the interior surface area of the mixing and dosing cup is at an angle of 10° or greater tangent to the exterior surface of the cup.

3. The method of claim 2, wherein the liquid dosage formulation comprises particles having a mass median particle size diameter of about 90 microns or less.

4. The method of claim 3, wherein the liquid dosage formulation comprises particles having a mass median particle size diameter of about 50 microns or less.

5. The method of claim 4, wherein the medicinal compound is selected from the group consisting of Amoxicillin Amoxicillin trihydrate and clavulanate potassium combination Cephalexin Clindamycin hydrochloride Doxycycline monohydrate Enrofloxacin Methimazole and Trimethoprim and sulfadiazine combination.

6. A method for the preparation and administration of a liquid dosage formulation from a solid dosage form of a medicinal compound and an aqueous diluent comprising: combining the solid dosage form and the aqueous diluent in a single-use mixing and dosing cup having an abrasive interior surface to form a mixture, agitating the mixture to form the liquid dosage formulation, and administering the liquid dosage formulation to a patient in the single-use mixing and dosing cup.

7. The method of claim 6, wherein about 10% to about 99% of the interior surface area of the mixing and dosing cup is at an angle of 10° or greater tangent to the exterior surface of the cup.

8. The method of claim 7, wherein the liquid dosage formulation comprises particles having a mass median particle size diameter of about 90 microns or less.

9. The method of claim 8, wherein the liquid dosage formulation comprises particles having a mass median particle size diameter of about 50 microns or less.

10. The method of claim 7, wherein the mixing and dosing cup further comprises a mixing blade attached to an external motor.

11. The method of claim 10, wherein the mixture is agitated by operation of the mixing blade.

12. The method of claim 7, wherein the medicinal compound is selected from the group consisting of Acetazolamide
Allopurinol
Amoxicillin
Captopril
Metronidazole
Rifampin and
Spironolactone.

* * * * *